(12) United States Patent  
Judd et al.

(10) Patent No.: US 7,254,436 B2  
(45) Date of Patent: Aug. 7, 2007

(54) DYNAMIC MAGNETIC RESONANCE ANGIOGRAPHY

(75) Inventors: Robert M. Judd, Chapel Hill, NC (US); Raymond J. Kim, Chapel Hill, NC (US); Enn-Ling Chen, Chapel Hill, NC (US)

(73) Assignee: Heart Imaging Technologies, LLC, Durham, NC (US)

( * ) Notice: Subject to any disclaimer, the term of this patent is extended or adjusted under 35 U.S.C. 154(b) by 148 days.

(21) Appl. No.: 10/449,252

(22) Filed: May 30, 2003

(65) Prior Publication Data

US 2004/0254452 A1 Dec. 16, 2004

(51) Int. Cl.
*A61B 5/055* (2006.01)

(52) U.S. Cl. ...................... 600/410; 600/419
(58) Field of Classification Search ............. 600/410, 600/419, 420; 324/307, 309, 306
See application file for complete search history.

(56) References Cited

U.S. PATENT DOCUMENTS

| | | | | |
|---|---|---|---|---|
| 4,716,367 A | * | 12/1987 | Patz | 324/309 |
| 5,337,749 A | * | 8/1994 | Shimizu | 600/419 |
| 6,307,368 B1 | * | 10/2001 | Vasanawala et al. | 324/309 |
| 6,806,709 B2 | * | 10/2004 | Markl et al. | 324/309 |
| 6,814,280 B2 | * | 11/2004 | Miyoshi et al. | 324/319 |
| 2004/0113613 A1 | * | 6/2004 | Markl et al. | 324/306 |
| 2004/0204643 A1 | * | 10/2004 | Jesmanowicz | 600/410 |

* cited by examiner

*Primary Examiner*—Ruth S. Smith
(74) *Attorney, Agent, or Firm*—Neal, Gerber & Eisenberg LLP

(57) ABSTRACT

A method for creating a magnetic resonance angiography (MRA) image including the steps of acquiring a magnetic resonance image in which a predetermined slice is excited using a train of radiofrequency (RF) pulses; and acquiring image data between the RF pulses such that the excited slice is viewable from a side view rather than from a face view. An MRA image generated by the steps of acquiring a magnetic resonance image in which a predetermined slice is excited using a train of radiofrequency (RF) pulses; acquiring image data between the RF pulses; viewing a side view of the slice, including dynamic spins within and exiting the slice.

18 Claims, 4 Drawing Sheets

| REAL SITUATION | TRADITIONAL IMAGING | NEW TECHNIQUE |
|---|---|---|
| Slice with blood vessel passing through  Flowing blood | Slice excited by SSFP  and viewed en face | Slice excited by SSFP  but viewed from side |

# DYNAMIC MAGNETIC RESONANCE ANGIOGRAPHY

BACKGROUND OF THE INVENTION (1) Field of the Invention

The present invention relates generally to magnetic resonance imaging and, more particularly, to a new magnetic resonance imaging method having angiographic applications.

(2) Description of the Prior Art

Magnetic resonance angiography (MRA) refers to the use of magnetic resonance imaging (MRI) for the specific purpose of examining blood vessels. MRA has many important clinical applications relating to the detection of blockages and other abnormalities that would otherwise require invasive procedure(s) to identify relevant information for diagnosis and treatment. The advantages of using MRI for MRA applications rests primarily on the basis of its non-invasive character and in the fact that it does not involve radiation and/or the use of potentially harmful contrast agents to perform the required tests. Currently, X-ray angiography is the standard technique used to detect stenoses in the artery but requires ionizing radiation and a contrast agent dye which can be damaging to kidneys.

Currently, all forms of MRA performed without a contrast agent are based on one of two physical principles: time-of-flight and phase contrast. However, the information gained from traditional MRA images does not typically provide enough information to replace existing angiographic testing procedures and the information gained therefrom. Specifically, traditional MRA techniques produce still-frame images whereas x-ray angiography produces cine images (movies) which portray the temporal filling of the blood vessels as the contraction of the heart pushes blood forward into the vessels.

Thus, there remains a need for an MRA based upon an MRI image that provides additional data and/or information for improved diagnostic testing without requiring invasive procedure, radiation, and/or contrast agents.

SUMMARY OF THE INVENTION

The present invention is directed to an MRA image that provides information for improved diagnostic testing without requiring invasive procedure, radiation, and/or contrast agents.

In a preferred embodiment, a new MRA technique is used that is based upon a different physical principle than that of the prior art as set forth hereinabove. As such, the present invention has intrinsic advantages compared to techniques based upon time-of-flight and phase contrast MRAs.

Preferably, the method and image captured thereby according to the present invention involve using traditional MRI process steps for general imaging, differing, however, with the three main steps for realizing the present invention: changing the viewing direction; creating a refocussing condition; and compensating the gradient waveforms for motion during imaging. The MRI according to the present invention is reprogrammed to excite the same plane or slice in space, but is viewable at the side so that the spins exiting the slice due to blood flow through a blood vessel now can be seen as well in the MRA, i.e., blood in the aorta can be seen to flow into the renal arteries in cine projection images of just the blood. Typically, a 16 cm lateral view is enough to view most important arteries in a chest, as in an angiography. While the image quality of the present invention is not quite as good as prior art methods, the same information is obtained without requiring the invasive procedure, contrast agents, radiation, and the like, as with the prior art.

The present invention is further directed to a method for creating an MRA image that includes information relating to the visualization of the content of blood vessels.

Accordingly, one aspect of the present invention is to provide a method for creating an MRA image including the steps of acquiring a magnetic resonance image in which a predetermined slice is excited using a train of radiofrequency (RF) pulses and acquiring image data between the RF pulses such that the excited slice is viewable from a side view rather than from a face view.

Another aspect of the present invention is to provide an MRA image generated by the steps of acquiring a magnetic resonance image in which a predetermined slice is excited using a train of radiofrequency (RF) pulses; acquiring image data between the RF pulses; viewing a side view of the slice, including dynamic spins within and exiting the slice.

These and other aspects of the present invention will become apparent to those skilled in the art after a reading of the following description of the preferred embodiment when considered with the drawings.

DETAILED DESCRIPTION OF THE PREFERRED EMBODIMENTS

Figure 1:
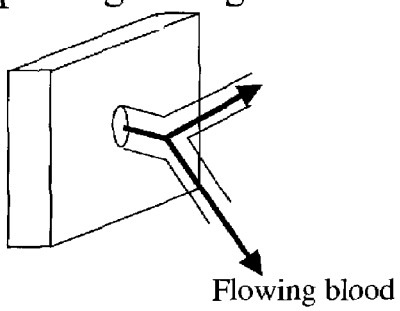
FIG. 1 is a schematic view of a comparison of viewing directions, including person embodiment, prior art perspective, and the side view perspective according to the present invention.
Figure 1:
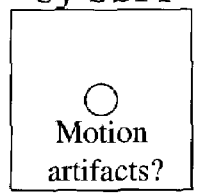
Figure 1:
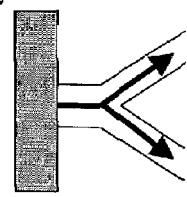

In the following description, like reference characters designate like or corresponding parts throughout the several views. Also in the following description, it is to be understood that such terms as "forward," "rearward," "front," "back," "right," "left," "upwardly," "downwardly," and the like are words of convenience and are not to be construed as limiting terms.

By way of additional background for the present invention, steady state free precession (SSFP) is an MRI term known in the art that relates to the phenomenom that, during imaging, the magnetization of the spins within the body can be made to refocus during the period of time between the acquisition of one line of raw data to the next line of raw data captured during testing. Due to this refocusing, magnetization placed on the transverse plane during a single radiofrequency (RF) excitation will effectively add to the magnetization of the next excitation. After many lines of data have been acquired, the transverse magnetization reaches what is referred to as a steady state. One of the intrinsic advantages of steady state MRI is that the absolute value of transverse magnetization created using SSFP techniques is often on the order of fifty percent (50%) of the theoretical maximum signal that can be achieved. Techniques that do not employ SSFP typically harness less than ten percent (10%) of the theoretical maximum.

During magnetic resonance imaging a slice of the person's body, i.e., a section of predetermined thickness, for example on the order of about 10 mm thick, is selected in such as way that only those spins located inside the slice are excited. In other words, spins that are forever located outside the section of predetermined thickness, or the slice, yield no signal for the MRI. Therefore, the magnetization that is created by MRI techniques is physically located only in the excited slice.

A key component of the method according to the present invention is that when blood flows in the body of the person being tested in a section of predetermined thickness being considered under the MRI, i.e., when blood flows through the imaging slice of the person's body for the MRI method, spins that were excited within that slice will remember or retain that excitation for a period of time even after leaving the slice. An important component of this "memory" effect is that MRI techniques which refocus magnetization from line-to-line, such as SSFP, allow spins outside the slice to continue to yield signal even though they no longer experience the slice-selective excitation. This period of "memory" time is approximated to be on the order of a few hundred milliseconds for typical MRI equipment as of the time of the present invention. Accordingly, spins that were in the slice but later exit the excited slice due to blood flow retain or remember that excitation and will continue to yield a signal for a period of time after exiting the slice. This "memory" time is a significant fraction of the cardiac cycle (heart beat) thereby allowing visualization of flowing blood due to heart contraction.

Ordinarily the signal produced by the spins that were in the slice but later exit the slice due to blood flow, hereinafter referred to as dynamic spins, are not of interest according to traditional MRI applications represented in the prior art because the focus of the MRI is on the excited slice for the purpose of providing imaging of body tissues located only within that slice. As such, the prior typically teaches away from the present invention. Accordingly, the signal associated with the dynamic spins is either ignored or intentionally suppressed because they often produce image artifacts.

However, in the method and images created thereby according to the present invention, these dynamic spins provide information that is significantly important for the MRA application. Importantly, another key component of the present invention is that the signal associated with dynamic spins, i.e., spins initially located in the excited slice but which later leave the slice due to blood flow, can be directly visualized if the slice is viewed from the side rather than en face, which is essential to the preferred embodiment of the present invention. It is this change of view or perspective of viewing the MRI that provides the additional information vital to enhanced MRA applications. This change of view or perspective of the slice is preferably achieved by changing the MRI gradient waveforms.

When the dynamic spins are viewed from the side, importantly, the only spins yielding a signal are those associated with the blood flow, i.e., the content of the blood vessels is directly visualized thereby. Accordingly, this approach according to the method and images created thereby of the present invention provides a new form of MRA that is based on a physical principle fundamentally different than those of the prior art, including time-of-flight and phase contrast techniques. The present invention provides for a method to compensate the gradient waveforms for motion of the dynamic spins during imaging, since such motion can shorten the "memory" time if not appropriately accounted for.

Preferably, the method and image captured thereby according to the present invention involve using traditional MRI process steps for general imaging, however, with the three main steps for realizing the present invention: changing the viewing direction; creating a refocussing condition; and compensating the gradient waveforms for motion during imaging. The MRI according to the present invention is reprogrammed to excite the same plane or slice in space, but is viewable at the side so that the spins exiting the slice due to blood flow through a blood vessel now can be seen as well in the MRA, e.g., the aortic fill into renal arteries can be seen as a projection image of just the blood. Typically, a 16 cm lateral view is enough to view most important arteries in a chest, as in an angiography. While the image quality is not quite as good as prior art methods, the same information is obtained without requiring the invasive procedure, contrast agents, radiation and the like, as with the prior art.

Preferably, the method according to the present invention for providing an MRA includes three main steps in addition to those traditionally used in MRI methods: changing the viewing direction; creating a refocussing condition; and compensating the gradient waveforms for motion during imaging. Furthermore, in step 1, changing the viewing direction of the MRI from a traditional en face viewing direction to a side view that more closely corresponds to the real situation of a person's blood vessel being considered under the MRI for MRA applications, is illustrated in FIG. 1. According to the present invention, the MRI view direction can be changed to a side view by playing the readout gradient on the slice gradient axis as detailed in the pulse sequence timing diagram shown in FIG. 2. Note that the x-axis (Gx) gradient, typically used for data readout, is not used at all because the readout gradient waveform is now played on the slice axis (Gz). In step 2 according to the present invention, the refocussing condition is created and maintained using standard techniques known to one of ordinary skill in the art to which the invention relates. In step 3, compensating the gradient waveforms for motion during imaging, through-plane motion is desirable for the technique to work effectively. However, the motion itself will cause loss of signal due to unintended accumulation of phase as the spins move through the gradients required for imaging. This problem of unintended phase accumulation due to motion is well known in the art, and specific techniques to avoid it are known as well. Preferably, in the present invention, avoiding unintended phase accumulation is provided according to known techniques, which are incorporated herein by reference in their entirety, such as, by way of example and not limitation, the typical solution to null the first moment of each gradient waveform such that any spins moving with constant velocity will accumulate no error. The timing and gradient shown in the timing diagram of FIG. 2 were carefully chosen to null the first moment of the slice and read axes as well as the phase axes. In the case of the phase axes, the moment is nulled at the center of each RF pulse.

The present invention includes a method for creating a magnetic resonance angiography (MRA) image including the steps of: acquiring a magnetic resonance image in which a predetermined slice is excited using a train of radiofrequency (RF) pulses; and acquiring image data between the RF pulses such that the excited slice is viewable from a side view rather than from a face view. The method may further include the step of acquiring a magnetic resonance image in which the excited slice includes select events and readout events that are played on the same gradient axis and/or the step of acquiring a magnetic resonance image in which the excited slice includes select events and phase encode events that are played on the same gradient axis. In one embodiment of the present invention, one or more gradient waveforms rewind magnetization prior to each subsequent radiofrequency (RF) excitation pulse and/or one or more gradient waveforms may compensate for motion.

Preferably, the image data are sampled using at least one coordinate system, preferably the coordinate system being selected from the group consisting of a Cartesian coordinate system, a non-Cartesian coordinate system, a radial coordinate system, and a spiral coordinate system.

In the method according to the present invention, the phase of the RF excitation pulses are either not changing or the phase of the RF excitation pulses are changed in a pattern which can be described mathematically, such as a repeating pattern.

A magnetic resonance angiography (MRA) image generated by the steps of acquiring a magnetic resonance image in which a predetermined slice is excited using a train of radiofrequency (RF) pulses; acquiring image data between the RF pulses; viewing a side view of the slice, including dynamic spins within and exiting the slice. Furthermore, the MRA image according to present invention creates an image that is usable for an x-ray angiography alternative in which blood vessels are viewed as a true "projection" image without the need for post-processing of the image data.

Figure 2:
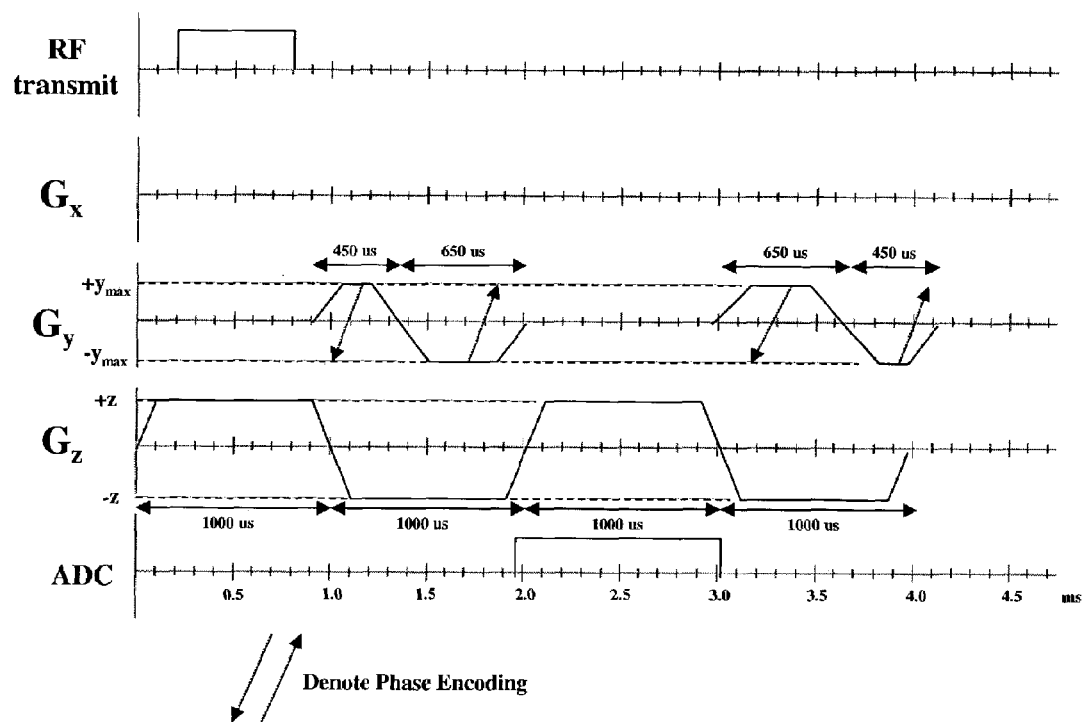
FIG. 2 is a graph showing one possible MRI pulse sequence according to an embodiment of the present invention.

Referring now to the drawings in general, the illustrations are for the purpose of describing a preferred embodiment of the invention and are not intended to limit the invention thereto. FIG. 1 is a schematic view of a comparison of viewing directions, including person embodiment, prior art perspective, and the side view perspective according to the present invention. Notably, the person embodiment or real situation shows a slice to be captured by an MRI imaging process with a blood vessel passing through the slice and flowing blood indicated to be passing through the blood vessel and the slice, and then leaving the slice more closely resembles the new technique of MRA according to the present invention than the traditional imaging view in the center of FIG. 1 wherein the excited slice is viewed en face with no possibility of indicating any MRI data associated with flowing blood that can be construed to represent, depict, or otherwise provide a visualization of the blood vessel outside the slide, in particular after exiting the slice. FIG. 2 is a graph showing phase encoding according to an embodiment of the present invention.

Figure 3:
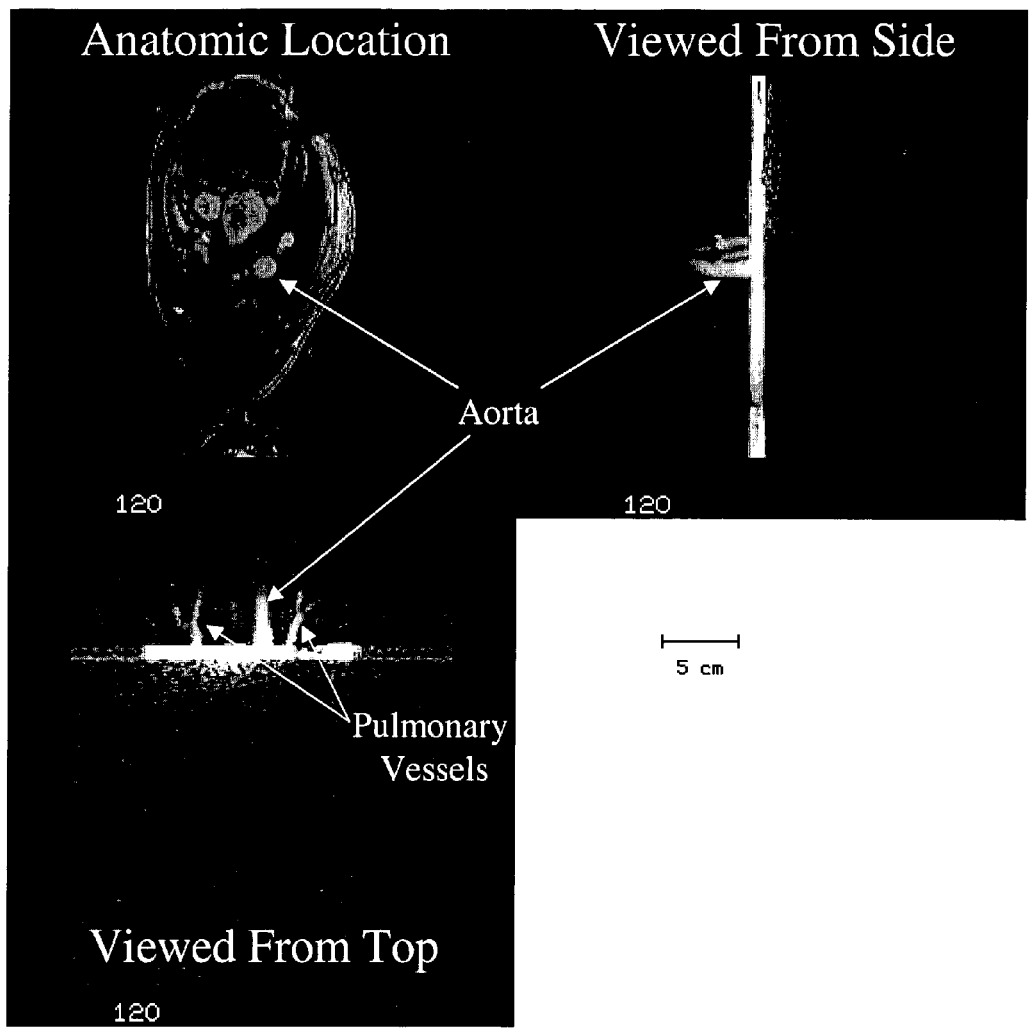
FIG. 3 is a magnetic resonance image view according to the present invention.

FIG. 3 is a magnetic resonance image view showing a side view and a top view associated with an anatomic location corresponding to the images acquired according to the present invention. FIG. 3 shows an example of one implementation of the method and image according to the present invention. An anesthetized dog was imaged at a location just below the heart in which the aorta and pulmonary vessels pass through the slice of the MRI. The blood within these vessels is clearly visualized from two different view directions. More particularly, in FIG. 3, the aorta and pulmonary vessels are identified from the images produced by dynamic spins that have moved in and through and then exited the excited slice that is the initial subject of the MRI data capture process as set forth hereinabove.

Figure 4:
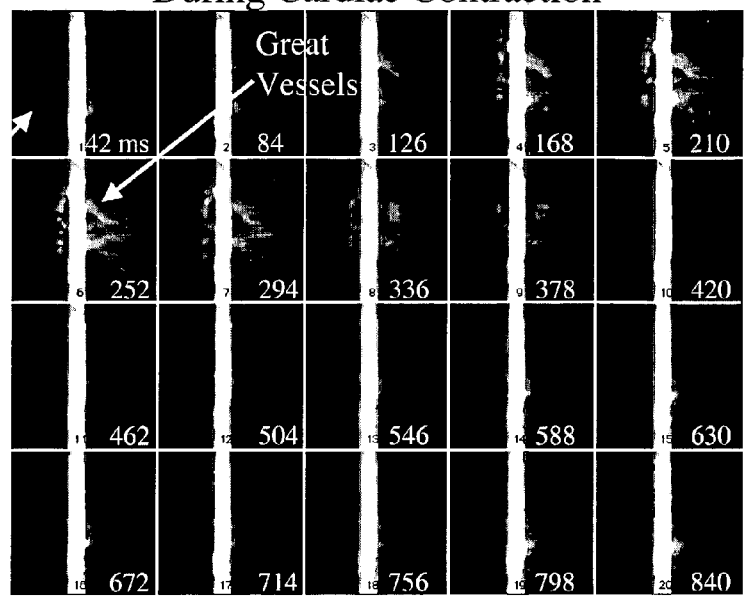
FIG. 4 is another magnetic resonance image view according to the present invention.
Figure 4:
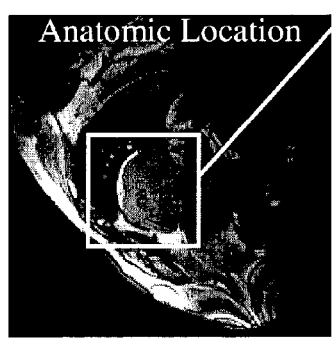

FIG. 4 shows an example of a different implementation of the method and image according to the present invention. More particularly, FIG. 4 is another magnetic resonance image view according to the present invention, however, it shows a side view with the function of time during cardiac contraction, with an anatomic location indicated therefore. A patient was imaged under MRI at a location just at the top of the heart. When viewed from the side as shown in FIG. 4, the great vessels above the heart can be visualized. Unlike in FIG. 3, however, images are shown as a function of time during cardiac contraction. The vessels fill during systole (126 through 336 milliseconds after the ECG r-wave) but not during diastole (378 through end). By measuring the distance blood has traveled within the vessels and dividing by time, blood flow velocity can be determined and used for MRA data testing and diagnostic applications.

Advantages of the present invention compared to prior art time-of-flight and phase contrast MRA include the following: signal from tissues surrounding the blood vessels does not have to be suppressed since tissues outside the slide were never excited; similar to x-ray angiography, the vessels are viewed as a true "projection" image without post-processing of the image data; similar to x-ray angiography, the vessels are viewed in a cine loop (movie) depicting temporal filling of vessels with blood; once outside the slice, the direction of motion is irrelevant unlike phase contrast MRA in which separate acquisitions are required for each spatial direction (x,y,z); and only one image acquisition is required, unlike phase contrast MRA which requires two acquisitions.

The method and image of the present invention are expected to have commercial applications in the following areas, which are listed by way of example and not limitation: imaging any blood vessel in the body; measuring vessel dimensions on blood vessel projections to determine the magnitude of obstructions; measuring blood velocities; measuring dimensions of the coronary arteries by placing the scan plane across the aortic root; determining coronary flow reserve as an index of stenotic severity by comparing the filling length of each coronary artery before versus after pharmacologic vasodilation (note that in this application, it is unnecessary to determine the diameter of the vessel suggesting that much poorer spatial resolution would be acceptable compared to applications in which vessel dimensions need to be determined); imaging software applications for scanner manufacturers.

Certain modifications and improvements will occur to those skilled in the art upon a reading of the foregoing description. All modifications and improvements have been deleted herein for the sake of conciseness and readability but are properly within the scope of the following claims.

We claim:

1. A method for noninvasive angiography, comprising the steps of:
    exciting a predetermined slice of a vascular region to coherently excite protons in fluid moving through the vascular region;
    acquiring at least one magnetic resonance image (MRI) of the vascular region while maintaining phase coherence of the protons; and
    projecting the at least one MRI onto a projection plane normal to the slice to view the vascular region within, and downstream of the slice.

2. The method according to claim 1, wherein excitement of the slice is performed using a train of RF pulses that occur in resonance with the frequency at which the fluid passes through the predetermined slice so as to coherently excite the protons.

3. The method according to claim 1, wherein the vascular region is visible on the projection plane as a movie formed by repetitive acquisition of MRI's between RF pulses.

4. The method according to claim 1, wherein the vascular region is visible up to about 16 cm downstream of the slice.

5. A method for noninvasive angiography, comprising the steps of:

exciting a predetermined slice of a vascular region using a train of radiofrequency (RF) pulses to coherently excite protons in fluid moving through the vascular region;

acquiring at least one magnetic resonance image (MRI) of the vascular region between the RF pulses while maintaining phase coherence of the protons; and projecting the at least one MRI onto a projection plane normal to the slice to view the vascular region within, and downstream of the slice.

6. The method according to claim 5, wherein the train of RF pulses occur in resonance with the frequency at which the fluid passes through the predetermined slice so as to coherently excite the protons.

7. The method according to claim 5, wherein phase coherence of the protons is maintained during acquisition of the at least one MRI using a gradient waveform having a zero first-order moment about the slice gradient axis and about the phase gradient axis.

8. The method according to claim 7, wherein the gradient waveform rewinds magnetization of the fluid between RF pulses.

9. The method according to claim 5, wherein projection of the at least one MRI onto the projection plane is created by playing a readout gradient waveform of the at least one MRI on the slice gradient axis.

10. The method according to claim 5, wherein the projection of the at least one MRI onto the projection plane is performed without post-processing the at least one MRI.

11. The method according to claim 5, wherein the vascular region is visible on the projection plane as a movie formed by repetitive acquisition of MRI's between RF pulses.

12. The method according to claim 11, wherein the vascular region is visible up to about 16 cm downstream of the slice.

13. A method for noninvasive angiography, comprising the steps of:

creating a refocussing condition while compensating the gradient waveforms for motion by exciting a predetermined slice of a vascular region using a train of radiofrequency (RF) pulses that are in resonance with the frequency at which fluid passes through the slice so as to coherently excite protons in the fluid moving through the vascular region;

acquiring at least one magnetic resonance image (MRI) of the vascular region between RF pulses while maintaining phase coherence of the protons;

changing the viewing direction by projecting the at least one MRI onto a projection plane normal to the slice to view the vascular region within, and downstream of the slice; and viewing the vascular region as a movie formed by repetitive acquisition and projection of the at least one MRI.

14. The method according to claim 13, wherein phase coherence of the protons is maintained during acquisition of the at least one MRI using a gradient waveform having a zero first-order moment about the slice gradient axis and about the phase gradient axis.

15. The method according to claim 14, wherein the gradient waveform rewinds magnetization of the fluid between RF pulses.

16. The method according to claim 13, wherein projection of the at least one MRI onto the projection plane is created by playing a readout gradient waveform of the at least one MRI on the slice gradient axis.

17. The method according to claim 13, wherein the projection of the at least one MRI onto the projection plane is performed without post-processing the at least one MRI.

18. The method according to claim 13, wherein the vascular region is visible up to about 16 cm downstream of the slice.

* * * * *